Figure 1:
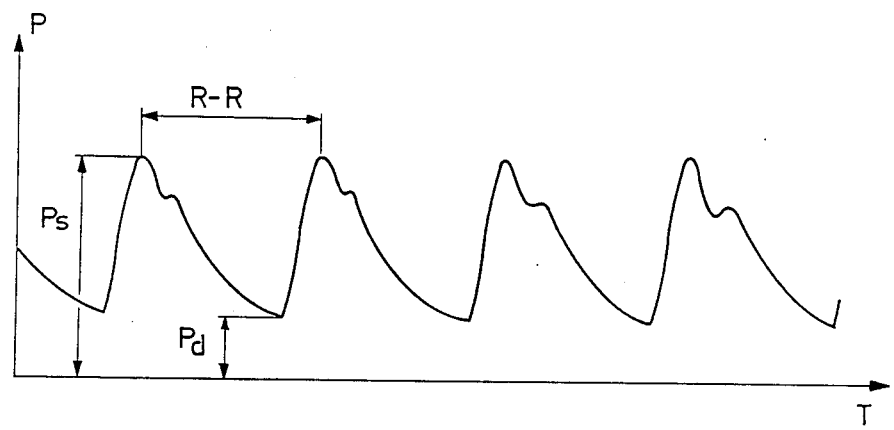

United States Patent [19]

Gedeon et al.

[11] Patent Number: 4,788,982

[45] Date of Patent: Dec. 6, 1988

[54] DEVICE FOR DETERMINING DEPTH OF ANAESTHESIA

[75] Inventors: Andras Gedeon, Täby; Lars-Erik Lindblad, Sollentuna, both of Sweden

[73] Assignee: ICOR AB, Bromma, Sweden

[21] Appl. No.: 3,035

[22] Filed: Jan. 13, 1987

[30] Foreign Application Priority Data

Jan. 23, 1986 [SE] Sweden ............................ 8600289

[51] Int. Cl.$^4$ .............................................. A61B 5/02
[52] U.S. Cl. .................................... 128/670; 128/666; 128/700; 128/672
[58] Field of Search ....................... 128/670–671, 128/672, 700, 696, 687, 706, 664–667

[56] References Cited

U.S. PATENT DOCUMENTS

| | | | |
|---|---|---|---|
| 4,248,241 | 2/1981 | Tacchi | 128/671 |
| 4,404,974 | 9/1983 | Titus | 128/670 |
| 4,510,944 | 4/1985 | Porges | 128/671 X |
| 4,519,395 | 5/1985 | Hruchesky | 128/671 |

Primary Examiner—Kyle L. Howell
Assistant Examiner—Angela D. Sykes
Attorney, Agent, or Firm—Browdy and Neimark

[57] ABSTRACT

A device for determining the depth of anaesthesia of a patient, the device including an optical measuring means (1) for measuring on a part (2) of the patient an optical parameter such as transmission or reflection, which is influenced by the circulation of the blood through this part of the patient's body, and to produce an electric signal which varies in accord with this parameter. This signal is related to the periodic variations in the blood-pressure of the patient and thus has a frequency which coincides with the heart frequency of the patient and a maximum amplitude and a minimum amplitude which are related respectively to the systolic and diastolic blood-pressure of the patient. The signal is applied to signal processing circuits (3) which determine the variation in the period of the signal ($\Delta$(R-R)) and the variation in its maximum amplitude ($\Delta P_{max}$) or minimum amplitude ($\Delta P_{min}$) or in the difference between its maximum and minimum amplitudes ($\Delta(P_{max}-P_{min})$) and construct a magnitude (K) which is proportional to the variation in the period of the signal or is preferably proportional to the ratio between the variation in the period of the signal and the variation in the maximum amplitude or minimum amplitude of the signal or in the difference between the maximum and minimum amplitudes. This magnitude (K) is presented as a measurement of the depth to which the patient has been anesthetized.

6 Claims, 1 Drawing Sheet

U.S. Patent  Dec. 6, 1988  4,788,982

DEVICE FOR DETERMINING DEPTH OF ANAESTHESIA

The present invention relates to a device for determining the depth of anaesthesia of a patient.

When administering an anaesthetic to a patient, it would be advantageous if the depth to which the patient is anaesthetized could be monitored readily in a continuous and non-invasive fashion. Unfortunately, there are today no known means which enable this to be done.

This deficiency in the art, however, has now been rectified with the device according to the invention having the characterizing features set forth in the accompanying claims.

The invention is based on knowledge of the blood-pressure control system of the human body. The sensitivity of this control system can be expressed as the ratio between the change in temporal distance between two mutually sequential heart beats (the so-called R-R-interval) and the change in the systolic blood-pressure associated therewith. The sensitivity K of the blood-pressure control system of the human body can thus be expressed as:

$$K = \frac{\Delta(R-R)}{\Delta P_s} \quad (1)$$

where $\Delta(R-R)$ is the change in the R-R-interval of the heart s activity and $\Delta P_s$ is the change in the systolic blood-pressure. In the accompanying drawing, FIG. 1 illustrates schematically a curve which shows the arterial blood-pressure P of a human being as a function of the time T, and in which the R-R-interval, the systolic blood-pressure $P_s$, and the diastolic blood-pressure $P_d$ are also shown.

Experiments have been conducted in which the sensitivity parameter K was measured by intentionally influencing the blood-pressure of a human subject, by injecting into the subject such drugs as those which have an effect on the blood-pressure, for example phenylephrine, whereafter the resultant changes in the systolic blood-pressure $P_s$ and in the heart frequency, i.e. the R-R-interval, were also measured. During these experiments K-values in the order of about 15-25 msec/torr have been established with the subject in a conscious state. It could also be established that the K-value decreases strongly under anaesthetic with the majority of inhalent anaesthetics used today, such as halothane, enfluorane and isofluorane for example.

Consequently, the present invention is based on the fundamental conception of using the aforesaid K-value as a means of measuring the depth to which a patient has been anaesthetized.

It will be understood, however, that it is not possible to this end to determine the K-values by injecting into the patient such drugs as those which affect his/her blood-pressure, as with the aforedescribed experiments. Consequently, in accordance with the invention, the K-value is determined by measuring the spontaneous variations in the heart frequency and the blood-pressure constantly occurring, this procedure constituting the second fundamental concept of the invention. It is known, inter alia, that breathing activity gives rise to both variations in the blood-pressure and in heart frequency, these variations having a periodicity which corresponds to the breathing frequency. Thus, there is found at least this natural disturbance of the system capable of enabling the K-value to be determined under anaesthetic and therewith the conscious state of the nerve system, i.e. the depth to which the patient has been anaesthetized.

Investigations have been made which indicate that the variation in heart frequency alone, i.e. $\Delta(R-R)$, could possibly provide a measure useful in determining the depth of anaesthesia of a patient. Consequently, it is conceivable, in accordance with the invention, to determine, as a measure of the depth of anaesthesia of a patient, solely a magnitude which is proportional to the variation of the heart frequency of a patient, i.e.

$$K \sim \Delta(R-R) \quad (2)$$

However, in order to determine the depth of anaesthesia unequivocally and reliably under varying clinical conditions, it is necessary to determine the ratio between the variation in heart frequency and the variation in blood-pressure. Thus, in accordance with the invention, there is determined to great advantage a magnitude which is proportional to this ratio, i.e.

$$K \sim \frac{\Delta(R-R)}{\Delta P} \quad (3)$$

where $\Delta P$ is the variation in blood-pressure.

It will be understood that, in principle, the variation in blood-pressure can be determined with respect to the blood-pressure at any given point whatsoever under the period of the blood-pressure curve, wherewith, however, the systolic blood-pressure $P_s$ should afford the best result, although the diastolic blood-pressure $P_d$ can also be used. The advantage afforded by these blood-pressures is that both can be safely detected. Accordingly, there is advantageously determined in accordance with the invention, a magnitude which is proportional to the ratio between the variation in heart frequency and either the variation in the systolic blood-pressure or the variation in the diastolic blood-pressure, i.e.

$$K \sim \frac{\Delta(R-R}{\Delta P_s} \quad (4)$$

or $$K \sim \frac{\Delta(R-R)}{\Delta P_d} \quad (5)$$

Since the variations in the systolic blood-pressure $P_s$ are greater than the variations i the diastolic blood-pressure $P_d$, it is also possible to use the variation in the difference between systolic and diastolic pressure as a measure of the variation in blood-pressure, i.e. $\Delta(P_s-P_d)$. This can afford important advantages from the aspect of technical measuring procedures. Thus, in accordance with this aspect of the invention, there is determined a magnitude which can be expressed as $$K \sim \frac{\Delta(R-R)}{\Delta(P_s - P_d)} \quad (6)$$

Thus, in order to be able to determine a K-value continuously and non-invasively in accordance with one of the aforesaid relationships (2)-(6), as a measure of the depth of anaesthesia of a patient, it is necessary to measure both the heart frequency of the patient, and a parameter which is related to the blood pressure of the patient, so as to enable the variations in these two magnitudes to be determined. This is achieved readily and effectively in accordance with the invention, with the use of an optical measuring device or transducer with which it is possible to measure on a part of the body of the patient an optical parameter, such as reflection or transmission for example, which is affected by the blood circulation through said part and which will generate an electric signal which varies in accord with this parameter. Such an optical measuring transducer includes a light source from which light is directed onto a selected part of the body of a patient, and a photodetector which receives the light transmitted or reflected by the tissue located in the irradiated part of the body and generates an electric signal representative of the strength of the transmitted or reflected light. The measuring transducer is suitably applied to a part of the patient's body through which blood flows freely and where the skin is relatively thin, such as, for example, the finger tips, toes, ear lobes or the inside of the lips of a patient. The light transmitted or reflected by the tissue and received by the photo-detector will thus be influenced by the blood flowing through the tissue, and the electric signal produced by the photo-detector will exhibit a periodic variation similar to the blood-pressure curve of the patient illustrated in FIG. 1. The electric signal obtained from the optical measuring transducer thus has a periodicity which corresponds to the heart frequency of the patient, and a maximum amplitude and a minimum amplitude which are related to the systolic and the diastolic blood-pressure of the patient respectively. By suitable filtration, this signal can be made to represent effects which are dependent on the blood pressure control system.

Optical measuring transducers of this principle kind have long been known in the art and used in medical technology, and are found incorporated, for example, in such instruments as pulse-oximeters used to measure the oxygenation of the patient's blood. These known instruments, however, are used to measure the transmission or reflection of light from tissue through which blood flows, within different, selected wave-length ranges, since the degree of oxygenation of the blood influences the colour thereof and therewith the different wave lengths of the light transmitted or reflected by such tissue. An optical measuring transducer of this kind, however, can also be used in a device according to the present invention for determining the depth of anaesthesia of a patient, since the electrical output signal of the transducer will vary, in the aforesaid manner, in relation to the periodic variations in the patient's blood-pressure, such as to contain information relating to both the heart frequency of the patient and the systolic and diastolic blood-pressure of said patient.

In actual fact, significant practical and economic advantages can be obtained by using one and the same optical measuring transducer for both determinig the depth of anaesthesia of a patient, in accordance with the invention, and to measure the level of oxygenation of the patient's blood, thereby enabling information concerning the oxygenation of the blood and the depth of anaesthesia of the patient to be obtained with the aid of a single piece of apparatus incorporating but a single optical measuring transducer. It will be understood that the same instrument can also readily be used to provide information concerning the heart frequency of the patient.

Figure 2:
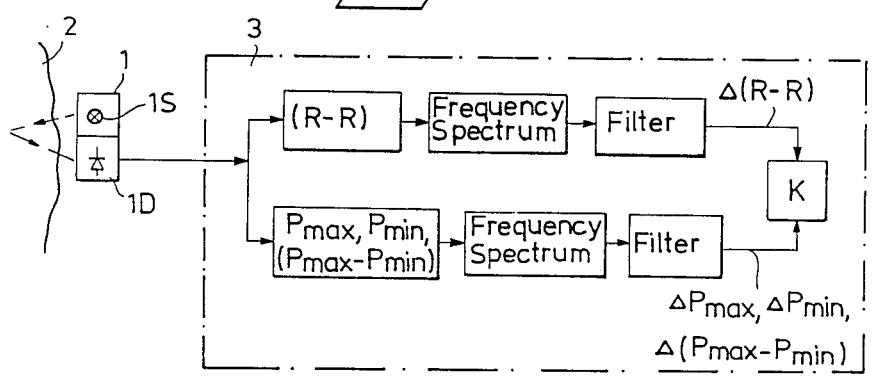

FIG. 2 of the accompanying drawing illustrates schematically the principle construction of a device according to the inention. This device thus incorporates an optical measuring transducer 1, which includes a light source 1S effective to transmit light onto a selected part or tissue 2 of a patient's body, shown only schematically in the Figure, and a photo-detector 1D which receives the light transmitted through the tissue 2 or, as with the illustrated embodiments, reflected by said tissue. The output signal produced by the photodetector 1D of the transducer 1 is passed to a signal processing unit 3, this output signal varying periodically in relation to periodic variations in the blood-pressure of the patient. This signal processor is constructed to detect the period of the received signal corresponding to the heart frequency of the patient i.e. (R-R), and also the value of the amplitude of the signal at a given point within this period, preferably its maximum amplitude $P_{max}$, related to the systolic blood-pressure of the patient, or its minimum amplitude, $P_{min}$, relating to the diastolic blood-pressure thereof, or to the difference between the maximum and minimum amplitudes, i.e. $P_{max}$-$P_{min}$. By suitable frequency analysis and filtration, the signal processing unit 3 then determines the magnitude of the variation in these parameters, i.e. $\Delta$(R-R) and $\Delta P_{max}$ or $\Delta P_{min}$ or $\Delta(P_{max}$-$P_{min})$, and on the basis thereof a K-value according to one of the expressions (2)-(6), this K-value being presented on some suitable display device as a measurement of the depth of anaesthesia of the patient.

Those skilled in this art will be aware that desired values of the variation in the period of the signal and the variation in its maximum amplitude or minimum amplitude, or the difference therebetween, can be determined in many different ways, by processing the output signal of the measuring transducer 1. One possible method is to determine the standard deviation of the parameter in question from its average value over a suitable number of heart beats. Another possible method is to analyse the variation frequency in said parameter and to determine the value of those components in the variation which lie within a given frequency range, wherewith a frequency range which includes the breathing frequency can be advantageously chosen, since it is known that the patient's breathing forms a source of spontaneous variations in the heart frequency and the blood-pressure of the patient. Thus, quite generally, there is determined the magnitude of the variation of the particular parameter within a frequency range lying between 0 and 0.5 Hz. Naturally, as those skilled in this art will appreciate, values representative of the variation in the frequency or period of the signal, ànd the variations in its maximum or minimum amplitudes can be derived from the output signal of the optical measuring transducer 1 also in ways other than those mentioned above.

We claim:

1. A device for determining the depth of anaesthesia of a patient, comprising:
 a measuring means for measuring, on a part of the patient's body, a periodically varying optical parameter of blood circulating through said part, said optical parameter having a frequency corresponding to the R-R interval of said patient and said optical parameter having an amplitude corresponding to the blood pressure of the patient, said measuring means including means for generating an electric signal which varies in accord with this parameter;

signal processing circuit means for receiving said signal generated by said measuring means, said circuit means including means for deriving from said signal a first value representative of variation in the length of successive R-R intervals, as well as means for deriving from said signal a second value representative of variation in the amplitude of said electric signal at a given point during each of said successive intervals, said circuit means also including means for obtaining a ratio of said first and second values;

whereby said ratio is taken as a measurement of the depth to which the patient is anesthetized.

2. A device as claimed in claim 1, wherein said second value is respresentative of the variation in the maximum amplitude of said electric signal during said successive R-R intervals.

3. A device as claimed in claim 1, wherein said second value is representative of the variation in the minimum amplitude of said electric signal during successive R-R intervals.

4. A device as claimed in claim 1, wherein said first and second values are determined within a frequency range of between 0 to 0.5 Hz.

5. A device as claimed in claim 1, wherein said first and second values are proportional to said variation in the length of successive R-R intervals and to said variation in the amplitude of said electric signal, respectively.

6. A device as claimed in claim 1, wherein said second value is representation of the variation in the difference between the maximum and minimum amplitudes of said electric signal during successive R-R intervals.

* * * * *